United States Patent [19]

Barranco, III

[11] Patent Number: 5,366,885

[45] Date of Patent: Nov. 22, 1994

[54] METHOD AND KIT FOR TESTING TUMORS FOR DRUG SENSITIVITY

[76] Inventor: Sam C. Barranco, III, 1005 Dartford Mews, Virginia Beach, Va. 23452

[21] Appl. No.: 895,782

[22] Filed: Jun. 9, 1992

[51] Int. Cl.$^5$ .......................... C12Q 1/02; C12Q 1/18
[52] U.S. Cl. ........................................ 435/6; 435/32; 435/29; 435/7.23; 435/967; 436/63; 436/64; 436/813
[58] Field of Search ................ 435/6, 32, 34, 29, 7.23, 435/967; 436/63, 64, 813, 87

[56] References Cited

PUBLICATIONS

Antman, K. H., "New Developments in Clinical Oncology: The Interdependence of Bench and Bedside", Cancer Research (Supp.), 51:5060s–5064s (1991).

Barranco, et al., "Heterogeneous responses in an *in vitro* model of human stomach cancer to anticancer drugs", Investigational New Drugs, 1:117–127 (1983).

Barranco, et al., "Treatment-induced Changes in Sensitivity in a Multiclonal Human Tumor Mixture Model *in Vitro*", Cancer Research, 48:2749–2755 (1988).

Barranco, et al., "Changes in drug sensitivity of a human astrocytoma clone previously treated with 1-(-2-chloroethyl)-3-(4-methylcyclohexyl)-1-nitrosourea *in vitro*", Investigational New Drugs, 6:293–298 (1988).

Barranco, et al., "Changes in Glutathione Content and Resistance to Anticancer Agents in Human Stomach Cancer Cells Induced by Treatments with Melphalan *in Vitro*", Cancer Research, 50:3614–3618 (1990).

Barranco, et al., "Relationship between glutathione levels and drug or radiation sensitivities in human gastric cancer cell lines *in vitro*", Investigational New Drugs, 2:29–36 (1991).

Bech-Hansen, et al., "Rapid Assays for Evaluating the Drug Sensitivity of Tumor Cells", J. Natl. Cancer Inst., 59:21–27 (1977).

Beck, W. T., "Do Anti-P-Glycoprotein Antibodies Have a Future in the Circumvention of Multidrug Resistance?", J. Natl. Cancer Inst., 83:1364–1366 (1991).

Bertelsen, et al., "Chemosensitivity Testing of Human Solid Tumors", Cancer, 53:1240–1245 (1984).

Carl J., "Drug-Resistance Patterns Assessed From Tumor Marker Analysis", J. Natl. Cancer Inst., 81:1631–1639 (1989).

Cole, et al., "A monoclonal antibody detecting cell surface epitope on some drug resistant human tumour cell lines", British J. Cancer, 62:14–16 (1990).

Dittrich, et al., "The human tumour cloning assay in the management of breast cancer patients", J. Cancer 52:197–203 (1985).

Efferth et al., "Rapid Detection Assays for Multidrug Resistance", Arzneimittel-Forshung/Drug Research, 38:1771–1774 (1988).

Engelholm, et al., "Chemosensitivity of Human Small Cell Carcinoma of the Lung Detected by Flow Cytometric DNA Analysis of Drug-Induced Cell Cycle Perturbations *In Vitro*", Cytometry, 7:243–250 (1986).

deFazio, et al., "Flow Cytometric Enumeration of Drug-resistant Tumor Cells", Cancer Research, 48:6037–6043 (1988).

Ferrero, et al., "Flow Cytometric Analysis of DNA Content and Keratins by Using CK7, CK8, CK18, CK19, and KL1 Monoclonal Antibodies in Beningn and Malignant Human Breast Tumors[1,2]", Cytometry, 11716–724 (1990).

Finlay, et al., "Cytokinetic factors in drug resistance of (List continued on next page.)

*Primary Examiner*—Toni R. Scheiner
*Attorney, Agent, or Firm*—Brumbaugh, Graves Donohue & Raymond

[57] ABSTRACT

Chemotherapy agents of interest are tested in untreated tumor cells and in tumor cells pretreated with buthionine sulfoximine (BSO) which reverses resistance related to elevated glutathione levels, and/or calcium channel blockers such as Verapamil which reduce resistance related to p-glycoprotein levels. The results of the several tests are then integrated to provide a predictor of tumor drug sensitivity and the potential utility of pretreatment regimens.

12 Claims, 7 Drawing Sheets

OTHER PUBLICATIONS

Lewis lung carcinoma: Comparison of cells freshly isolated from tumours with cells from exponential and plateau-phase cultures", British J. Cancer, 56:755–762 (1987).

Herweijer, et al., "A Rapid and Sensitive Flow Cytometric Method for the Detection of Multidrug-Resistant Cells", Cytometry, 10:463–468 (1989).

Johnston, et al., "Glutathione S-Transferase Activity, Sulfhydryl Group and Glutathione Levels, and DNA Cross-Linking Activity With Chlorambucil in Chronic Lymphocytic Leukemia", J. Natl. Cancer Inst., 82:776–779 (1990).

Kashani-Sabet, et al., "Detection of Drug Resistance in Human Tumors by in Vitro Enzymatic Amplification", Cancer Research, 48:5775–5778, (1988).

Kern, et al., "Development of a Miniaturized, Improved Nucleic Acid Precursor Incorporation Assay for Chemosensitivity Testing of Human Solid Tumors", Cancer Research, 45:5436–5441 (1985).

Kern, et al., "Highly Specific Prediction of Antineoplastic Drug Resistance With an In Vitro Assay Using Suprapharmacologic Drug Exposures", J. Natl. Cancer Inst., 82:582–588 (1990).

Kung, et al., "Cytotoxic Effects of Cell Cycle Phase Specific Agents: Result of Cell Cycle Perturbation", Cancer Research, 50:7307–7317 (1990).

Landberg et al., "Antibodies to Proliferating Cell Nuclear Antigen as S-Phase Probes in Flow Cytometric Cell Cycle Analysis", Cancer Research, 51:4570–4574 (1991).

Lee, et al., "Prediction of tumour sensitivity to 4-hydroperoxycyclophosphamide by a glutathione-targeted assay", British J. Cancer, 63:217–222 (1991).

van der Linden, et al., "Flow Cytometric DNA Content of Fresh Tumor Specimens Using Keratin-Antibody as Second Stain for Two-Parameter Analysis", 13:163–168 (1992).

Ling, V., "Does P-glycoprotein Predict Response to Chemotherapy?" J. Natl. Cancer Inst., 81:84–85 (1989).

Meitner, "The Fluorescent Cytoprint Assay: A New Approach to In Vibro Chemosensitivity Testing", Oncology, 5:75–88 (1991).

Mitchell, et al., "Glutathione as a Predictor of Tumor Response", in Prediction of Tumor Treatment Response, Chapman, et al., Pergamon Press, New York 157–174.

Moscow, et al., "Multidrug Resistance", J. Natl. Cancer Inst., 80:157–174 (1988).

Nair, et al., "Flow Cytometric Monitoring of Glutathione Content and Anthracycline Retention in Tumor Cells", Cytometry, 12:336–342 (1991).

Oguro, et al., "Dynamic analysis of changing features of tumor cells incubated with antitumor agents in vitro and its application for predictive activity assay of antitumor agents", Japanese J. Cancer Res., 76:131–141 (1985).

Rice, et al., "Quantitative Analysis of Cellular Glutathione by Flow Cytometry Utilizing Monochlorobimane: Some Applications to Radiation and Drug Resistance in Vitro and in Vivo", Cancer Research 46:6105–6110 (1986).

Scheithauer, et al., "New Screening System for Selection of Anticancer Drugs for Treatment of Human Colorectal Cancer", Cancer Research, 46:2703–2708 (1986).

Schroy III, et al., "New Chemotherapeutic Drug Sensitivity Assay for Colon Carcinomas in Monolayer Culture", Cancer Research, 48:3236–3244 (1988).

Shrivastav, et al., "An in Vitro Assay Procedure to Test Chemotherapeutic Drugs on Cells from Human Solid Tumors", Cancer Research, 40:4438–4442 (1980).

Silvestrini, et al., "Potentials of Cell Kinetics in the Management of Patients with Ovarian Cancers", Eur. J. Cancer., 28:386–390 (1992).

Schuurhuis, et al., "Potentiation of doxorubicin cytotoxicity by the calcium antagonist bepridil in anthracycline-resistant and -sensitive cell lines", Cancer Chemother Pharmacol, 20:285–290 (1987).

Treumer, et al., "Flow-cytometric Determination of Glutathione Alterations in Vital Cells by o-Phthaldialdehyde (OPT) Staining", Experimental Cell Research, 163:518–524 (1986).

Waalen, J. "Drug Resistance: A Little Help From Other Tissues: Two Drugs Appear to be Helpful Against Resistance to Chemo", Oncology Times Dec. (1986).

"New Trial at Fox Chase to Test Buthionine Sulfoximine Against Drug Resistance", Oncology, 3:132.

Chase, M. "Picking the Right Drug After Breast Surgery".

(List continued on next page.)

OTHER PUBLICATIONS

Gallagher, G. L., "Evolutions: The Cell Cycle", J. of NIH Research, 4:124–126 (1992).

Gazdar, et al., "*In Vitro* Assays for Predicting Clinical Response in Human Lung Cancer", in *Prediction of Tumor Treatment Respnse*, Chapman, et al., Pergamon Press, New York 175–186.

von Hoff, D., "Send this patient's tumor for culture and sensitivity", The New England Journal of Medicine, 308:154–155 (1983).

Hryniuk, et al., "Implications of Dose Intensity for Cancer Chemotherapy", Seminars in Oncology, 14:43–44 (1987).

McGuire, R., "New Game Plan for Tackling Drug Resistance", Oncology Times, Jun. (1990).

Stern, J., "Symposium Explores Ways to Overcome Mechanisms of Drug Resistance in Cells", Oncology Times, Dec. (1986).

Volm, et al., "Pretherapeutic Detection of Tumour Resistance and the Results of Tumour Chemotherapy", Europ. J. Cancer, 15:983–993 (1979).

Volm, et al., "Prediction of the clinical chemotherapeutic response of stage III lung adenocarcinoma patients by an *in vitro* short term test", British J. Cancer 57:198–200 (1988).

Volm, et al., "Relationship of DNA Ploidy to Chemoresistance of Tumors as Measured by *In Vitro* Tests", Cytometry, 11:406–410 (1990).

Weisenthal, et al., "Prediction of Drug Resistance in Cancer Chemotherapy: The Kern and DiSC Assays", Oncology, 5:93–118 (1991).

Wilson, et al., "Measurement of cell kinetics in human tumours *in vivo* using bromodeoxyuridine incorporation and flow cytometry", British J. Cancer, 58:423–431 (1988).

METHOD AND KIT FOR TESTING TUMORS FOR DRUG SENSITIVITY

The invention described in this application was made using U.S. Government funding under National Cancer Institute Grant No. 1-R01-CA 15397. The U.S. Government has certain rights under any patent granted hereon.

BACKGROUND OF THE INVENTION

This application relates to a method and kit for use in testing cells, and particularly tumor or leukemia cells, for drug sensitivity.

Chemotherapy agents are frequently employed in treatment of many forms of cancer. The theory underlying the use of these agents, which are all extremely cytotoxic, is that they will be more harmful to the rapidly dividing tumor cells than to the patient as a whole. In some cases, however, a given tumor either proves to be initially resistant to the chemotherapy agents administered or develops resistance over the course of treatment. This resistance, whether natural or induced, cannot be overcome by simply increasing the dosage because this may unacceptably increase the harmful side effects of the agent to the patient, and it therefore becomes necessary to completely change the treatment regime.

The harm to the patient from an aborted attempt at chemotherapy may be substantial. First, the patient has been physically injured to some extent by the administration of the chemotherapy agents and has not received much, if any, offsetting benefit. Second, in many cases, the cancer may progress during the period of ineffective treatment to a point where the therapy with the second-chosen group of agents comes too late to substantially prolong the patient's life. Accordingly, a method of determining the drug sensitivity profile of a given tumor prior to the administration of chemotherapy agents would be highly desirable.

Several tests have been disclosed whose goal is the prediction of resistance to chemotherapy agents. One of the earliest of these was based on the observation in 1954 that the ability of chemotherapy agents to reduce cellular metabolism could be monitored by measuring tetrazolium blue reduction by fresh tumor biopsy materials. (Black et al., J. Nat'l Cancer Inst. 14, 1147-1158 (1954)). Subsequently, assays have been proposed that rely on cloning of human tumor stem cells, (Salmon et al., N. Engl. J. Med. 298, 1321-1327 (1978)), on the uptake of radiolabeled thymidine by tumor cells in the presence and absence of the chemotherapy agent being tested (Kern et al., Int'l J. Cell Cloning 5, 421-431 (1987)); and on the differential staining properties of living and dead cells (Weisenthal et al., Oncology, 5, 93-103, (1991)).

Each of these assays provides a measure of predictability to the question of tumor drug resistance. Many of these assays take 7 to 21 days to complete, however, which in some cases is longer than many physicians are willing to wait before initiating chemotherapy. Furthermore, the reliability of these tests is sufficiently variable that not all physicians are willing to trust the test results. There thus exists an unfulfilled need for a predictive assay for drug resistance which provides rapid, reliable results for a spectrum of possible chemotherapy agents. It is an object of the present invention to provide such an assay.

SUMMARY OF THE INVENTION

The method of the invention involves parallel testing of each chemotherapy agent of interest in untreated tumor cells and in tumor cells pretreated either with buthionine sulfoximine (BSO) which reverses resistance related to elevated glutathione levels, or a calcium channel blocker such as Verapamil which reduces resistance related to p-glycoprotein levels. Thus, the method comprises the steps of: (a) obtaining a sample of normal tissue and a sample of tumor tissue from the patient; (b) measuring the baseline levels of glutathione (GSH) and p-glycoprotein (PGP), DNA index (content) and proliferation fraction (% $S+G_2M$ Phases) in a portion of each of the two samples; (c) dissociating a further portion of the tumor sample into 1-3 $mm^3$ fragments and suspending the dissociated tumor tissue in tissue culture medium; (d) dispensing suspended tumor cells into a plurality of vessels; (e) adding the calcium channel blocker to approximately one third of the vessels and adding BSO to a different approximately one third of the vessels and incubating under conditions suitable for cell growth for a period of time sufficient to achieve about an 80 to 90% reduction in GSH and PGP content (usually a 24 hour treatment, following which the cells are retested for GSH+PGP content); (f) adding the chemotherapy agent after the incubation period to a portion of the vessels containing the dissociated tumor cells in medium only or in medium plus the pretreatment agents, the remainder of the vessels serving as untreated controls; (g) incubating the suspended tumor cells in the presence of the chemotherapy agent for a further period of time sufficient to achieve an effect on cell division (cell cycle kinetics); (h) recovering the cells after incubation; and (i) evaluating the cell kinetics effects of the chemotherapy agent on the tumor cells in the presence and absence of BSO or calcium channel blocker pretreatments. The results of the several tests are then integrated to provide a predictor of tumor drug sensitivity and the potential utility of pretreatment regimens.

The method of the invention is advantageously performed using a kit containing the reagents used in the assay, i.e. BSO and a calcium channel blocker. The kit may also advantageously include a plurality of vessels, for example in the form of a microtiter plate, for performing the incubation steps. The reagents are advantageously packaged in individual units of the amount required for use in one vessel, and may in the case that the vessels are supplied with the kit be supplied already dispersed into appropriately labeled vessels. The kit may also include one or more chemotherapy agents, preferably prepackaged into dosage units of appropriate size for the vessels to be used in the test.

DETAILED DESCRIPTION OF THE INVENTION

The present invention is generally intended as a method for determining the drug sensitivity of tumor cells of an individual patient, although it will be appreciated that it could also be used to test the efficacy of new drug candidates against established cell lines. The first step in the procedure is obtaining an appropriate sample for testing. Preferred patient tumor samples for use in the present invention are those that have been obtained within 48 hours of beginning the test and stored at 5° C. to 10° C. in tissue culture medium such as HAM's F-10, or McCOY's 5-A with 10% fetal calf serum. The sample is preferably between 0.75 and 1 gram in weight after trimming to remove fat and necrotic tissue.

At the same time the sample of tumor tissue is obtained, a sample of normal tissue from the same organ is also obtained. This normal sample is preferably between 0.25 and 0.5 grams in weight, after trimming off any fat, and should be stored in the same manner as the tumor tissue.

At the commencement of the test procedure, the sample of tumor material is divided into two portions. One portion, approximately 0.2 g in weight, and the normal tissue sample are used for determination of baseline levels of GSH and PGP and the extent of DNA content and DNA synthesis occurring before treatment. The second portion of the tumor tissue is dissociated for use in the main assay.

Dissociation of the tumor tissue into small fragments may be achieved by first cutting the tissue into small pieces (4–5 mm$^3$) in the presence of tissue culture medium and then passing these pieces through a needle (e.g. a 26 gauge needle) using a syringe to form a suspension of uniform fragments of 1–3 mm$^3$. Other methods to obtain similarly dissociated suspensions (e.g. enzyme dissociation) may also be employed.

After dissociation, the tumor cell suspension is diluted as necessary with tissue culture medium to achieve a suspension containing about 20–40 fragments/ml. Small aliquots of the suspension are then transferred to a plurality of test vessels. Useful test vessels are the wells of a microtiter plate in which case about 0.4 ml or 4–8 fragments per microtiter well are transferred.

Figure 1:
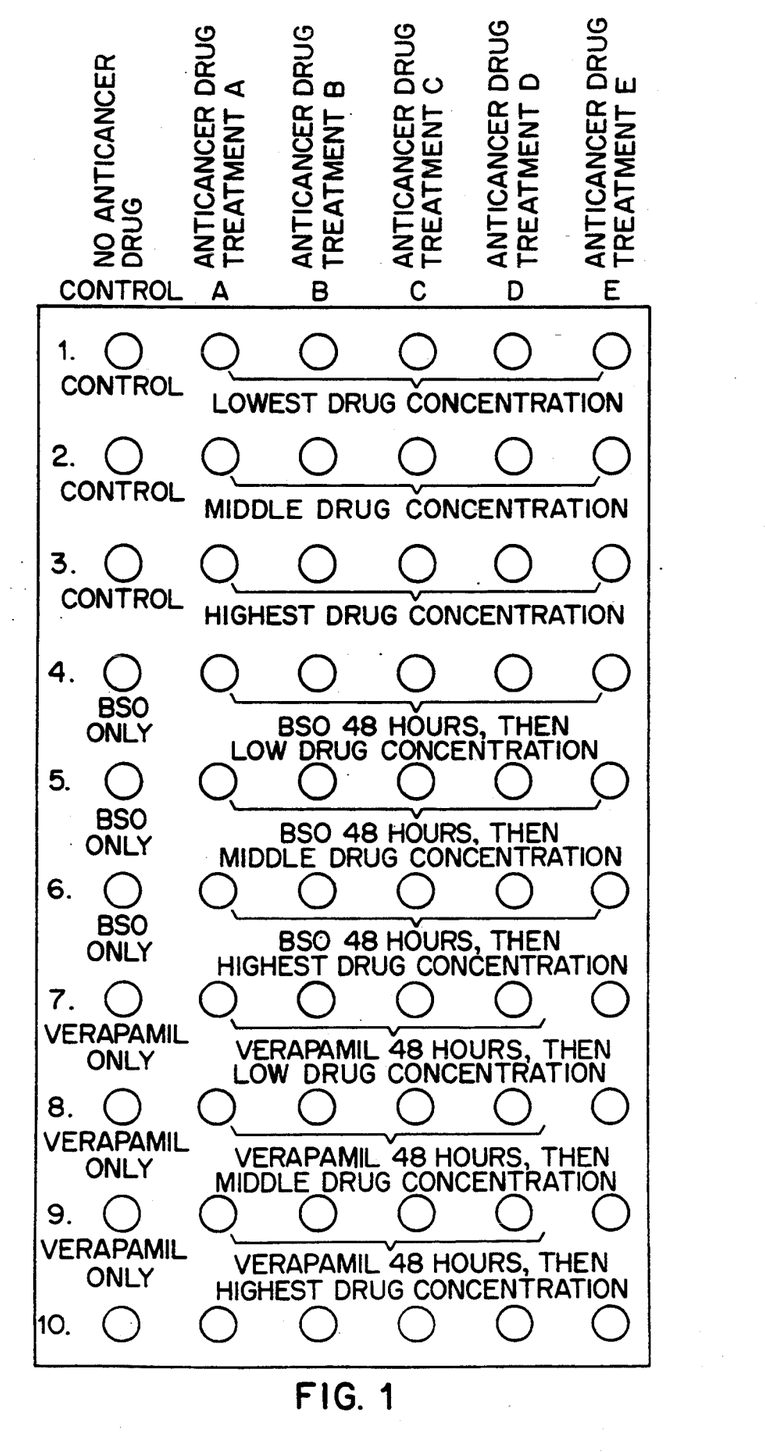
FIG. 1 shows schematically a testing apparatus for testing the sensitivity of a tumor to five drugs in accordance with the invention.

FIG. 1 shows a schematic view of a microtiter plate labeled for use in the present invention. 0.2 to 0.4 ml of tumor cell suspension is transferred into each of the 60 wells. Pretreatment agents BSO or Verapamil are then added to the wells in rows 4–6 and 7–9, respectively, as shown, and the material in the wells gently agitated. The tumor cells in the wells are then incubated under conditions conducive to cell growth until about 80 to 90% decreases in GSH and PGP concentrations are achieved. In general, incubation at 37° C. in a humidified incubator with an environment of 95% air and 5% $CO_2$ for periods of 24 to 48 hours is sufficient to achieve this goal.

After this initial incubation, the chemotherapy agents to be tested are added to the appropriate wells. In FIG. 1, each chemotherapy agent (A–E) is tested at three different dosage levels. Thus, well A1 is treated with the lowest concentration of drug A while well A3 is treated with the highest concentration of drug A. After addition of the chemotherapy agents, the tumor cells are incubated for an additional period of time, generally 2 to 48 hours, to allow time for a drug effect on cell growth (cell cycle kinetics). Permanent human cancer cell lines known to be sensitive or resistant to the anticancer drugs may be employed in each test as positive and negative controls for drug sensitivity and resistances, respectively. (Assays on these human cell lines would prove that each drug was active by producing appropriate effects in known sensitive or resistant cells).

After this second incubation the cells in each well are thoroughly rinsed and incubated in fresh growth media for about 24 hours to allow the cell kinetics blockade to be expressed. The cells are then tested for drug effects. First, cells and tissue fragments are recovered from the wells. Cells that have become attached to the walls of the vessel can be removed by treatment with trypsin (for example, 0.25% trypsin for 5 minutes). The recovered material is then dissociated into single cells, for example by treatment with 0.5% pepsin for 20 minutes at 37° C. (Zante et al., in *Pulse Cytophotometry*, European Press, Ghent, Belgium, (1976)). The resulting single cell suspensions are then subjected to three groups of tests.

First, the effect of the chemotherapy agent on cell kinetics is tested. Aliquots of each sample are treated with RNase (0.1%) and stained with a DNA stain (such as Ethidium bromide Mithromycin). The cells may also be counterstained with cytokeratin to distinguish cancer from normal cells to provide a two parameter assay on the DNA of the cancer cells, particularly in those cancer biopsies having low percentages of tumor cells (verified by pathologist) in order to distinguish between drug effects on tumor versus normal tissues (Ferrero et al., Cytometry, 11 716–724, (1990)). Then, using a flow cytometer, the S-phase and proliferation fractions (S+$G_2$M) are determined in accordance with the method of Guseman et al., J. Pulse Cytometry, 79–92 (1979). Changes in the S+$G_2$M phase fractions of the cell cycle in treated populations compared to controls indicate that the cells are sensitive to the anticancer agents.

The DNA Index or content may be determined using, for example, the method of Barlogie et al., Cancer Res. 38, 3333–3338 (1978) to confirm the cell kinetics data by comparing the amount of DNA synthesized in normal cell preparation and treated and untreated tumor cell preparations. Other methods such as BrdU incorporation to measure drug effects on DNA syntheses (Wilson et al. Br. J. Cancer, 58 pp. 423–431, (1988)) may also be employed.

The second test performed is the evaluation of BSO effect on GSH levels. GSH acts as a radical scavenger and inactivates drugs such as adriamycin, melphalan, Bleomycin, mitomycin C, the nitrosoureas, and x-rays before they can kill the cells. Thus, elevated GSH levels are a recognized cause of drug resistance. (Barranco, et al., Investigational New Drugs, 9, 29–36, (1991); and Barranco et al. Cancer Res., 50, 3614–3618, (1990)).

Aliquots of sample from the BSO treated control wells (BSO controls 4, 5 and 6 in FIG. 1) and an untreated control are stained with mercury orange or monochlorobimane (Nair et al. Cytometry 12, 336–342 (1991)) and evaluated using the flow cytometer to obtain mean channel fluorescence values. Alternatively, the enzymatic method of Tietze (Anal. Biochem. 27, 502–522 (1969)) may be used. In this method, tumor and normal tissue samples are homogenized in ice-cold 5% sulfosalicylic acid (e.g. using a polytron tissue homogenizer, and the sample debris spun down (e.g. at $10,000 \times g$ for 20 minutes). The supernatant is assayed immediately for total GSH using the Tietze cyclic reduction method (Anal. Biochem. 27, 502–522 (1969) or frozen at $-80°$ C. until assayed. Assays are advantageously performed in duplicate. When using cancer biopsies, verification of the presence and percentages of cancer cells in the populations studied will be provided by a pathologist.

The third test performed is the evaluation of the effect of Verapamil or other calcium channel blockers such as nifedipine and diltiazem on PGP levels. PGP acts as a pump and removes from the cells drugs such as Vincristine, Vinblastine, doxorubicin, Actinomycin D, Mitomycin C, etc., before they can kill the cells. Thus, elevated PGP levels may also be associated with drug resistance. (Riodan et al., J. Biol. Chem. 254, 12701–12705, (1979)).

In this test, cells from the treated control wells (Verapamil controls 7, 8 and 9 in FIG. 1) and an untreated control (well 3) are treated with PGP stains (for example, P-glycoCHEK C 219 from Centocor Diagnostics, Malvern, Pa.) and evaluated in the flow cytometer to obtain the mean channel fluorescence values.

Alternatively the third test (for PGP content) can be performed on tissue sections of treated tumor samples. This immunohistochemistry assay is performed with a monoclonal antibody that directly measures an external epitope of the mdr1-P-glycoprotein. Sensitive cells are negative for PGP. As a positive control for the sensitivity of this analysis, the CEMVLB-100 cell line which is resistant to Vinblastine can be used. A suitable negative control is the CEM cell line which is sensitive to the drug. Assays are performed in duplicate. When using cancer biopsies, verification of the presence and percentages of cancer cells in the population studied will be provided by a pathologist.

The interpretation of these three groups of tests is illustrated with reference to Tables 1 and 2 which show the results of a hypothetical three drug screening of a patient's tumor material.

As shown in Table 1, treatment with Drug A alone resulted in no change in cell kinetics. Thus, based on the cell kinetics data alone, Drug A is not a preferred choice for treatment. Additional information is provided, however, by the testing of BSO effects and GSH levels which reveals that the cause of the tumor's resistance to Drug A is probably the result of elevated GSH levels. Thus, if Drug A is to be used (for example, because it is expected that the patient will tolerate it well), BSO pretreatment should be used.

Although the patient in Table 1 shows elevated GSH levels, the tumor cells respond to treatment with Drug B, suggesting that the drug was not influenced by GSH and therefore, no drug resistance results. Drug B also proves to be effective even in the presence of elevated PGP levels. (Table 2). The tumor may therefore be treated directly with Drug B without pretreatment with BSO or Verapamil.

Drug C in Table 2 is illustrative of a drug which requires pretreatment with Verapamil to overcome resistance associated with elevated PGP levels. In conclusion, Drug B is the most effective and is not dependent upon GSH values or PGP activity to exert its effect on the cells. The patient will probably be resistant to Drugs A and C because of elevated GSH and PGP levels in the cancer cells. To be more effective, BSO must be given to the patient for at least 48 hours before Drug A and Verapamil must be administered for 48 hours before Drug C. It is likely that treatments to reduce resistance will be required each time before Drugs A and C are used.

In certain cases, for example, when the percentage of tumor cells in the test sample is low (below 60–70%), the presence of nontumor tissue may present a problem in interpretation of the results. For that reason, the test samples will be counterstained with cytokeratin antibodies (Biogenex Labs, San Ramon, Calif.) to distinguish carcinoma from normal tissue. Using a 2-parameter assay, the cell kinetics, GSH and PGP results can be obtained on tumor cells which have been identified by the cytokeratin. Such two-parameter assays are a valuable tool useful in overcoming problems of false-positive and false-negative results.

As shown in FIG. 1, the test is advantageously performed at three dosage levels of each chemotherapy agent: one approximately equal to normal dosages attainable in patients, one less than normal dosages by a factor of 2 to 3; and one greater than normal dosages by a factor of 10 to 100. In this way, relative sensitivity of tumor material can be gauged.

An advantage of the present assay is the number of internal checks that prevent erroneous interpretations of the results and thus provide a very high level of reliability. Thus, the assay involves treatment of both normal and tumor cells obtained from fresh biopsies with an anticancer drug, and testing for the presence of drug-induced cell cycle kinetics blockades by flow cytometry. The effects of a drug on cell cycle kinetics is correlated with two intracellular biochemical modulators of drug sensitivity and resistance—GSH and PGP. Together, the three tests act as a chemosensitivity panel.

The rationale for this cell kinetics test is that if a drug can get into the tumor cells, and remain active, without interference from GSH and PGP, to cause major perturbations in cell cycle kinetics, it is likely that it can kill the cells too. This relationship has been shown by Kung et al. (*Cancer Research* 50 pp. 7307–7317, 1990) and by the applicant's research. (Barranco et al., Invest. New Drugs, 4, 347–357, (1986); Barranco et al., Invest. New Drugs, 1 011–020, (1983); Barranco et al., Cancer Res. 48, 2749–2755, (1988)).

Figure 2A:
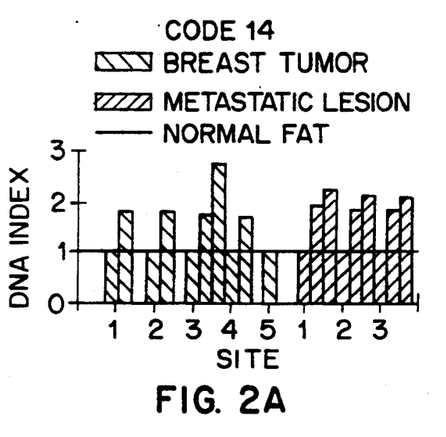
FIGS. 2 and 3 show normal variability in DNA and GSH contents at various sites within a tumor (primary and metastatic) as compared to normal values.
Figure 2B:
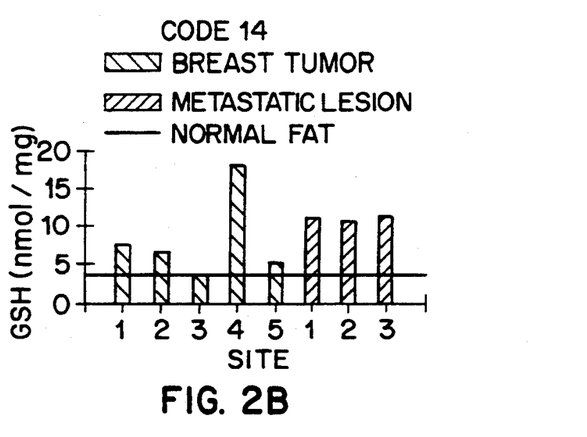
Figure 3A:
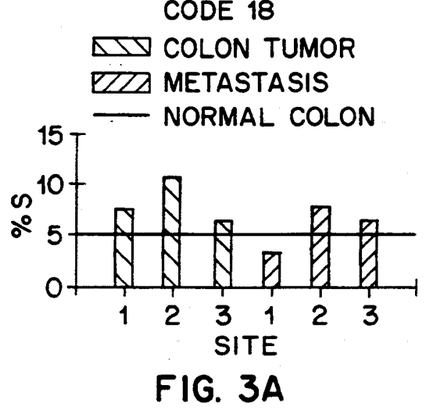
Figure 3B:
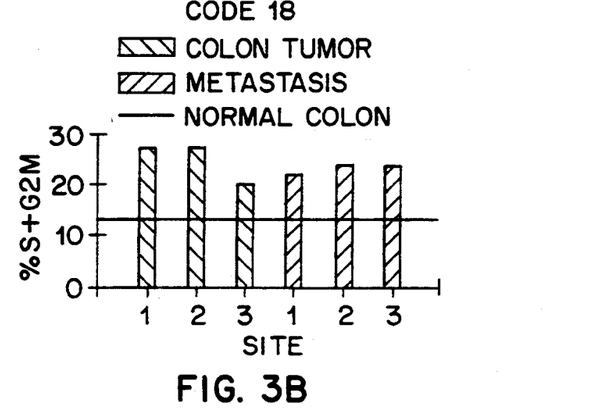
Figure 3C:
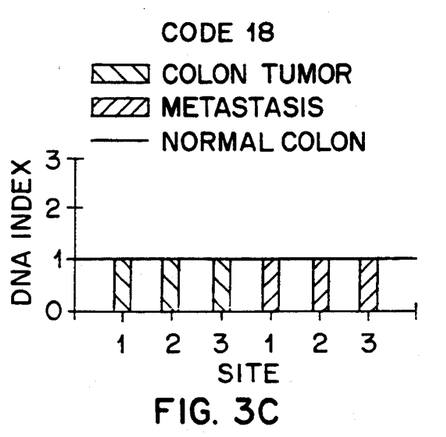
Figure 3D:
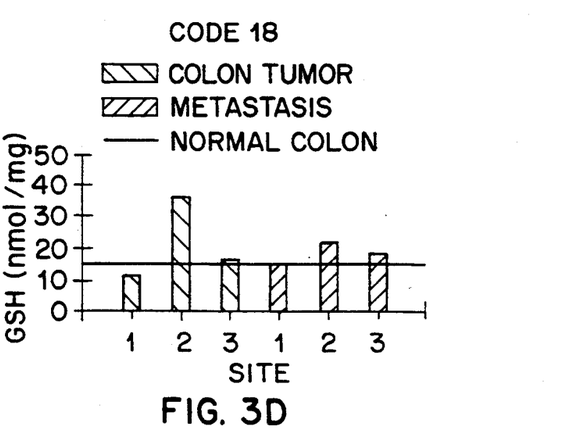

Taken alone, none of the tests employed provides a reliable indicator of the usefulness of a given drug because substantial variation in any one test can be observed depending on the site from which the sample is taken. This is reflected in FIGS. 2 and 3, which show test results for tissue samples from two actual patients. Furthermore, if only the cell kinetics test is done and no drug-induced cell cycle effects are observed, there would be no way of knowing whether the cells were truly resistant or just that the drug had decayed or for some other technical reason did not work properly. On the other hand, without the flow cytometry-based cell kinetics test, the GSH and PGP assays would be no more useful than those for DNA Index, proliferation fraction, or S-phase fraction in identifying patients who may be resistant to specific drug therapy, because none of these tests measures drug effects directly on the tumor cells. They are only correlated with patient survival length of time in a disease free state, regrowths of tumor or treatment failure.

In contrast, in the method of the invention, the effect of a specific drug on cell kinetics is always taken in the context of the other tests. By combining the cell kinetics test with the GSH and PGP assays, a possible explanation for the observed resistance may be obtained. These results would be confirmed by the reversal of resistance by treatment with either BSO or a calcium channel blocker. Once GSH and PGP levels were reduced, cell kinetics changes caused by an anticancer drug treatment would prove not only that the tumor cells were resistant to that drug (thereby confirming the first test), but would also give evidence that the cells could be made sensitive by the proper pre-treatment. Alternatively, the incorporation of the pyrimidine analogue BrdU into DNA of proliferating cells may be used to determine drug effects on the percentage of DNA synthesizing cells (Riccardi et al, Cancer Res. 48, 6238–6245, (1988)). This use of bivariate flow cytometry to measure BrdU incorporation and DNA content provides another means of confirming the drug-induced cell kinetics effects. Such four-tiered confirmatory testing [(1) cell kinetics vs (2) PGP and GSH levels vs (3) reversal of GSH and PGP resistance by BSO or Verapamil vs (4) BrdU] is an important means of overcoming problems with false-negative or false-positive results.

The reliability of the assay may be further improved by the use of cytokeratin to identify and distinguish tumor tissue from normal cells in the assay. This allows the results to be obtained and reported specifically on tumor tissue, without the contamination of background "noise" from normal cells and debris co-isolated with the tumor during the sample preparation. The use of BrdU to study the effects of anticancer drugs on DNA synthesis can provide an additional check on cell cycle effects. This gives the oncologist additional information on which to base a treatment plan for a specific patient, and moves one step closer to achieving the longstanding goal of individualized treatment plans for each cancer patient.

The method of the invention is advantageously performed using a kit adapted for this purpose. Such a kit will contain BSO and a calcium channel blocker, and optionally one or more of the following: (1) a set of vessels for performing the incubation steps; (2) one or more chemotherapy agents to be tested; (3) one or more reagents for staining the cells for flow cytometry, BrdU and cytokeratin assays; (4) one or more reagents for determining GSH levels and (5) one or more reagents for determining PGP levels. The reagents provided with the kit are advantageously provided in pre-measured amounts, particularly where a set of vessels is included in the kit. Further, the BSO and calcium channel blocker may be disposed within the vessels, if provided, for example, as a coating on the walls of a pre-labeled microtiter plate to be used in the assay.

EXAMPLE 1

Figure 4A:
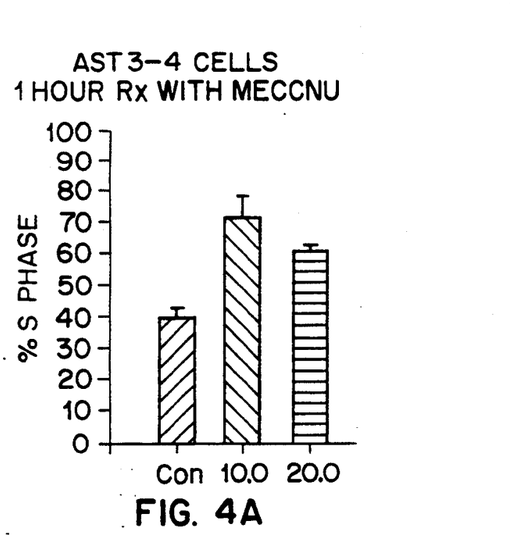
FIGS. 4, 5 and 6 show test data for the application of MeCCNU to a human tumor cell line (astrocytoma) cancer model.
Figure 4B:
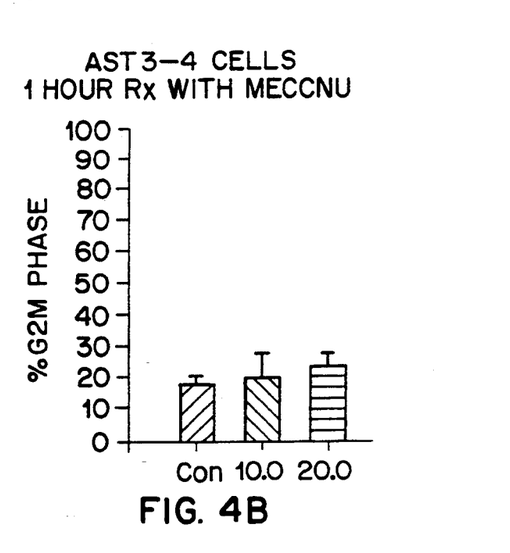
Figure 5A:
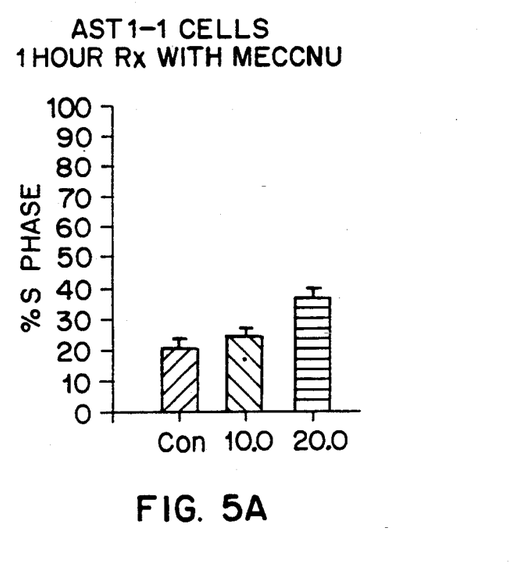
Figure 5B:
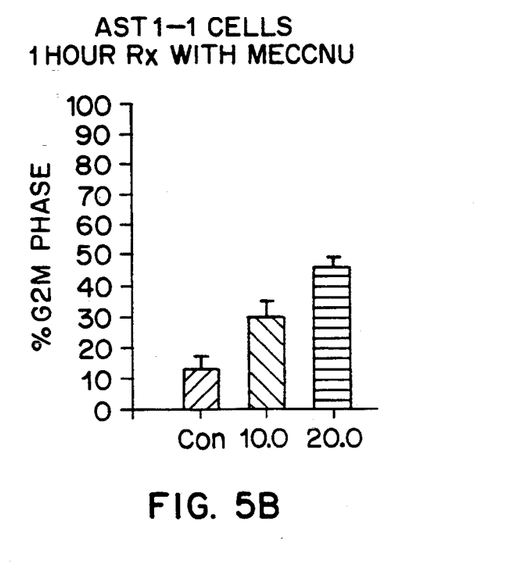
Figure 6:
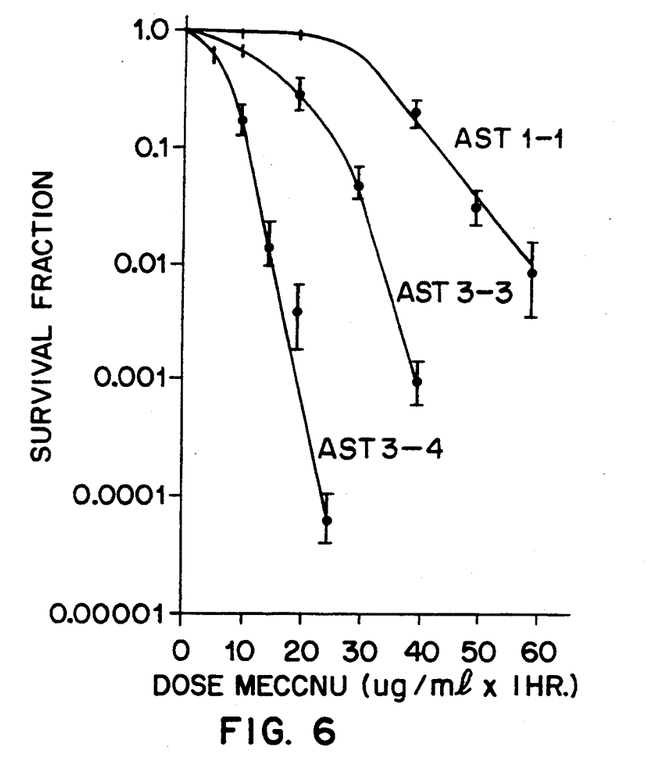

Two permanent cell line clones of a human astrocytoma (AST 3-4 and AST 1-1) were treated for 1 hour with the anticancer nitrosourea compound MeCCNU (with either 10 or 20 μg MeCCNU/ml). The cells were then washed with saline and incubated in fresh medium at 37° C. for 24 hours. They were prepared and assayed on the flow cytometer by the previously described method of Zante. The results in FIGS. 4–6 show that AST 3-4 was more sensitive than AST 1-1 to MeCCNU, and at a lower dose—75% increase in S-phase at 10 μg/ml versus a 10% increase in AST 1-1. This is significant since it is believed that a cell cycle delay in S-phase, i.e. an increase in the percentage of cells, is related to interruption of DNA synthesis which could lead to cell death. Delays in $G_2$ and M phases on the other hand are usually related only to cell progression effects unless supralethal doses are used, in which case $G_2M$ blockades are attributed to cell death. To obtain a larger kinetic response in AST 1-1, the dose had to be doubled to 20 μg/ml. However, doubling of the dose may not be possible in a cancer patient.

The $D_0$'s (a measure of the slopes of the survival curve) for MeCCNU were used to correlate with the kinetics results (small $D_0$=greater sensitivity). The $D_0$ for the AST 3-4 was 2.7 μg MeCCNU/ml for 1 hour versus 6.0 for AST 1-1, indicating that AST 3-4 was 2.2 times more sensitive. This is further supported by the dose response survival curves themselves (FIG. 6). At 10 μg/ml almost 90% of AST 3-4 cells were killed (0.1 or 10% survival); whereas no AST 1-1 cells were killed. Likewise at 20 μg/ml, 99.5% of AST 3-4 cells and no AST 1-1 cells were killed. As with the kinetics assays, higher doses did eventually have effects on AST 1-1 survival; however, to kill as many cells as were killed by 10 μg/ml in AST 3-4, a dose almost 5 times higher was required in the resistant AST 1-1 cells (FIG. 6). This shows the necessity for determining cell kinetics cut off values that would indicate which data would be acceptable as predictors of a tumor's response to a drug. In other words a tumor may exhibit some kinetics response to the drug, as AST 1-1 did; but the patient could not tolerate a 5 fold increase in the dose to achieve a better response exhibited by a more sensitive tumor. Establishing such minima and maxima would help to eliminate false positives or weakly sensitive responses as demonstrated by AST 1-1, and prompt the search for more effective drugs for that tumor.

In this case cell kinetics assays alone were inadequate. A more comprehensive understanding of the degree of resistance expressed by AST 1-1 may have been possible if GSH and PGP levels were known. Reversal of resistance by pretreatment with BSO or Verapamil may have made these cells more sensitive to drug treatment without a five fold increase in the dose.

EXAMPLE 2

Figure 7A:
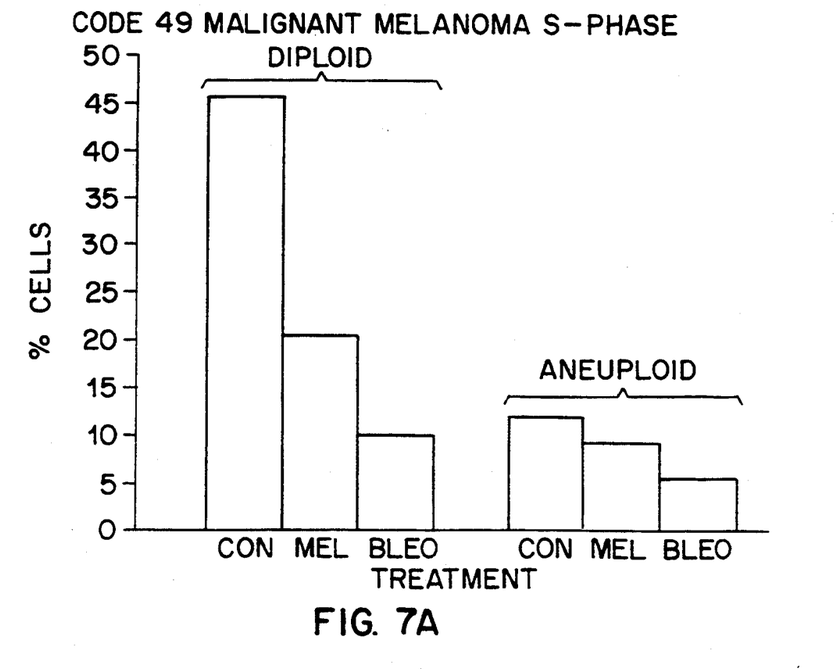
FIG. 7 shows results from testing of drug effects (Melphalan and Bleomycin) on a metastatic lesion of a malignant melanoma biopsy.
Figure 7B:
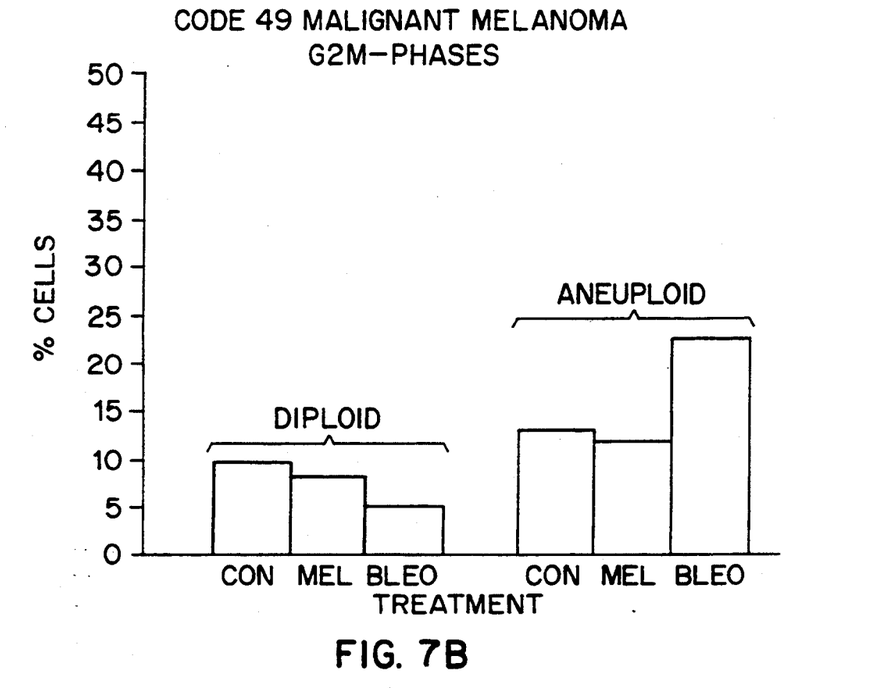

Normal and cancer tissues were obtained from a metastatic lesion of a malignant melanoma patient (code 49) and processed within 24 hours with anticancer agents: Melphalan (Mel) (5 μg/ml) and Bleomycin (Bleo) (50 μg/ml). In FIG. 7, the results of cell-cycle kinetics studies are shown. The % cells in S-phase in untreated control cells was 45% (diploid fraction). Cells treated with Mel or Bleo had reductions in S-phase fractions to 20% and 10%, respectively. Aneuploid cells also exhibited reductions, although smaller. Diploid cells in $G_2M$ phases also exhibited slight decreases in treated populations. These data, taken together, suggest a massive $G_1$ block caused by drug treatment. Aneuploid $G_2M$ phase cells exhibited a $G_2$ blockade (23% in treated vs 12% in control cells). The overall interpretation suggests that the drugs were able to enter and exert an effect on the tumor. Assays on the tissues (by the Tietze method described earlier) indicated that the GSH values in the tumor and normal tissues were in the normal ranges. Thus, the kinetics results were validated by the GSH data to support the conclusion of probable effectiveness.

EXAMPLE 3

Figure 8:
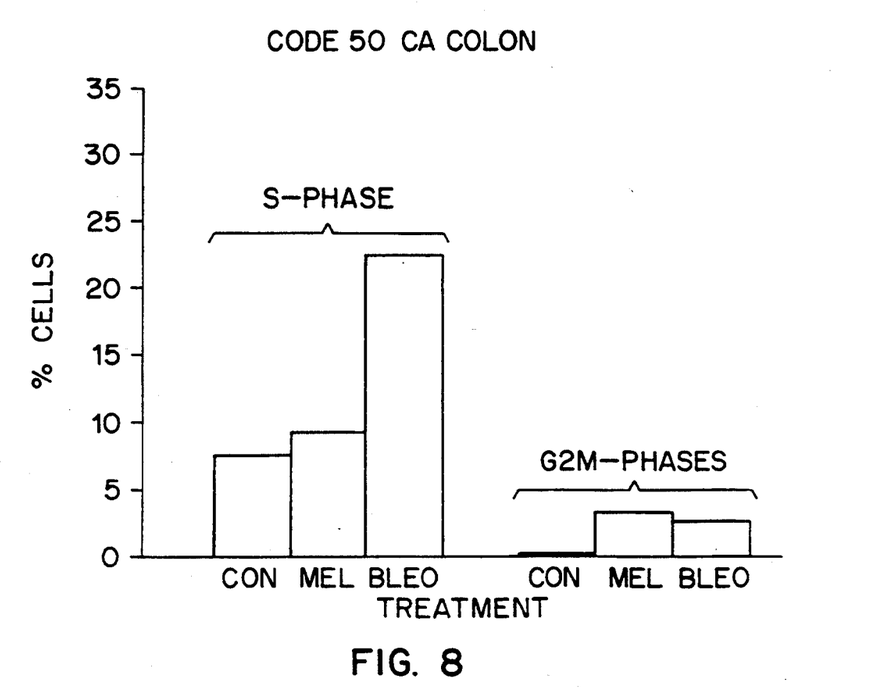
FIG. 8 shows results from testing drug effects (Melphalan and Bleomycin) on a diploid adenocarcinoma of the colon obtained by biopsy.

In FIG. 8, data on drug effects on a diploid adenocarcinoma of the colon are presented. Both Mel & Bleo treatments caused increases in $S+G_2M$ phases of the cell cycle. When compared to the melanoma patient, these data demonstrate the variable effects caused by drug treatment in different patients and with different tumors. In the first patient, the largest cell cycle effects were due to arrest of cells in the $G_1$ phase. In this patient, cell cycle arrest occurred in $S+G_2M$ phases and the GSH values for this tumor were also in the normal range. This suggests that this tumor would be sensitive to both Melphalan and Bleomycin.

EXAMPLE 4

Figure 9A:
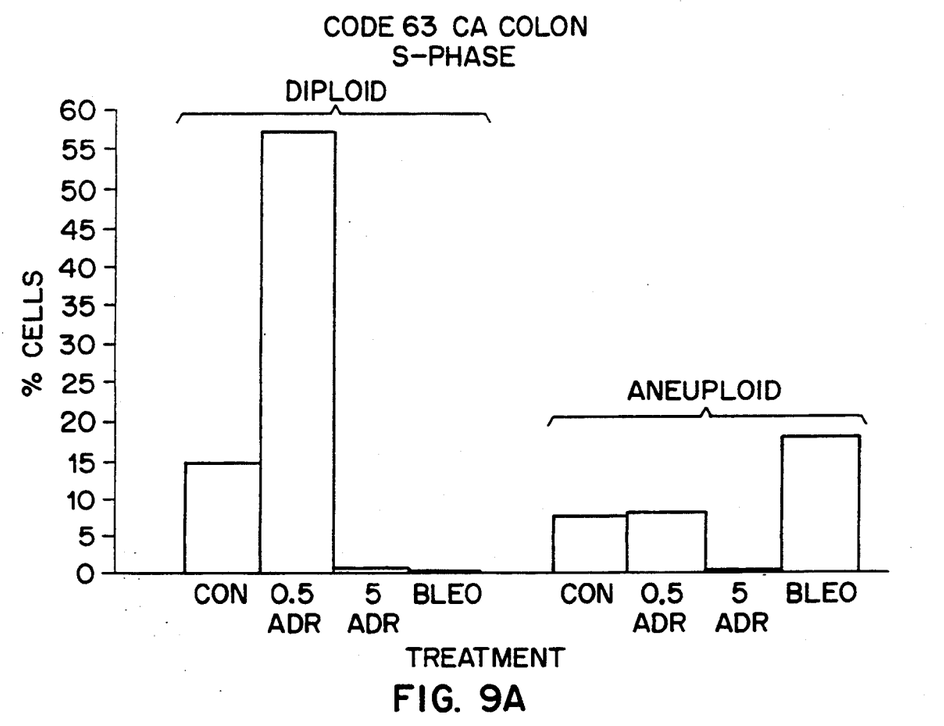
FIG. 9 shows results from testing adriamycin or Bleomycin effects on a biopsy of an adenocarcinoma of the colon.
Figure 9B:
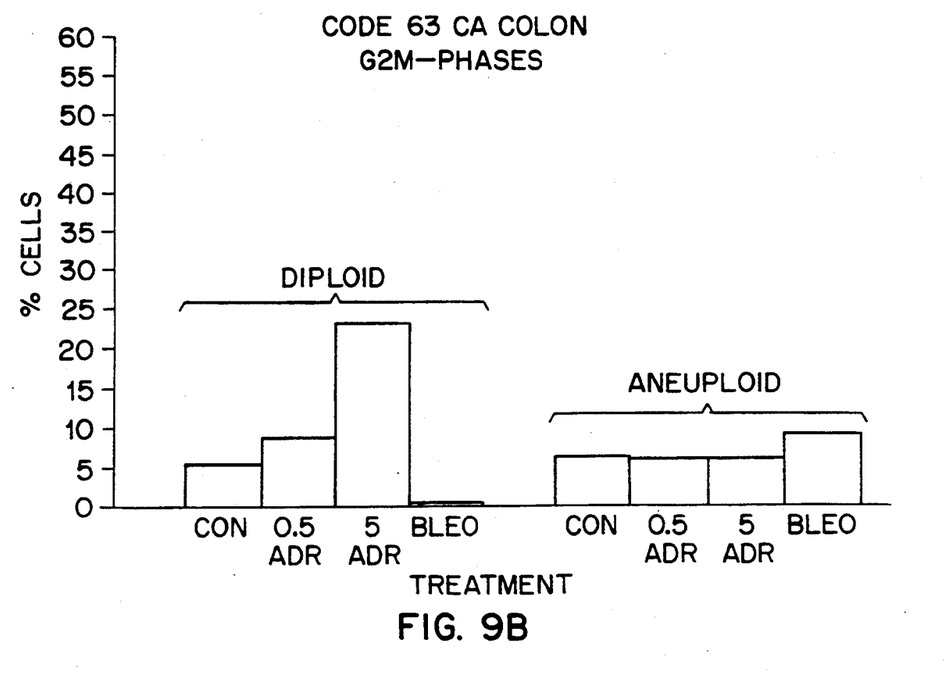

In FIG. 9, the results of two different doses of Adriamycin (0.5 or 5 µg/ml for 24 hours) on an adenocarcinoma of the colon are shown. In the diploid cohort of cells, the lowest Adria dose caused an S-phase arrest; the higher Adria dose caused a $G_1$ phase arrest. Bleo also caused a $G_1$ arrest. In the aneuploid segment of this tumor, the lower Adria dose had no effect (compared to untreated controls), while the higher Adria dose still produced a $G_1$ blockade. Bleo caused a large S-phase block in these aneuploid cells. $G_2M$ phase blockades occurred with both Adria doses in diploid cells. Diploid cells exposed to Bleo showed a large decrease in $G_2M$ phase cells, probably the result of the $G_1$ blockade. Aneuploid cells treated with both Adria doses were not affected. A slight $G_2M$ phase block was observed after Bleo treatment. Since GSH values were in the normal range, no interference by GSH on drug effects were expected or observed.

EXAMPLE 5

Figure 10A:
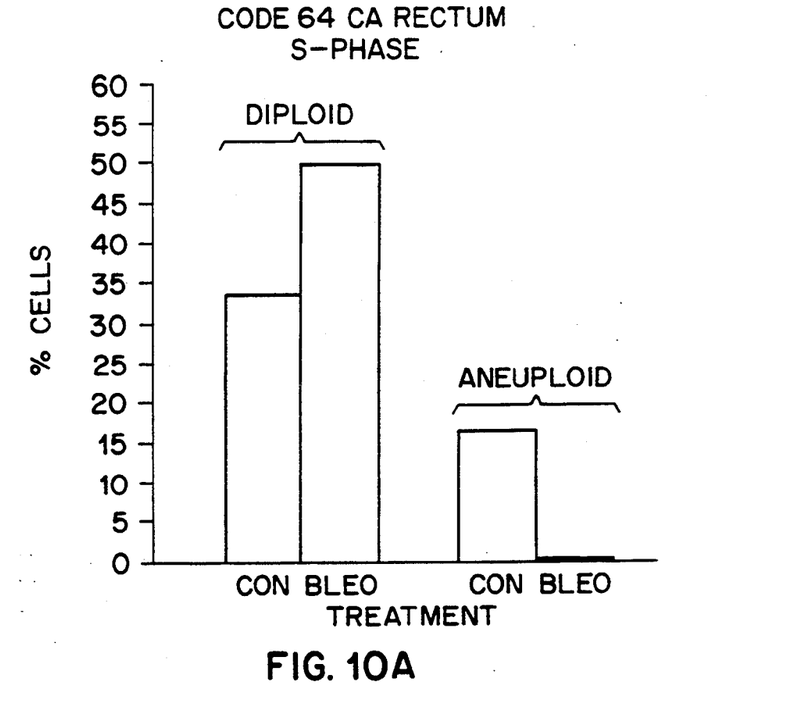
FIG. 10 shows results from testing bleomycin effects on a biopsy of an adenocarcinoma of the rectum.
Figure 10B:
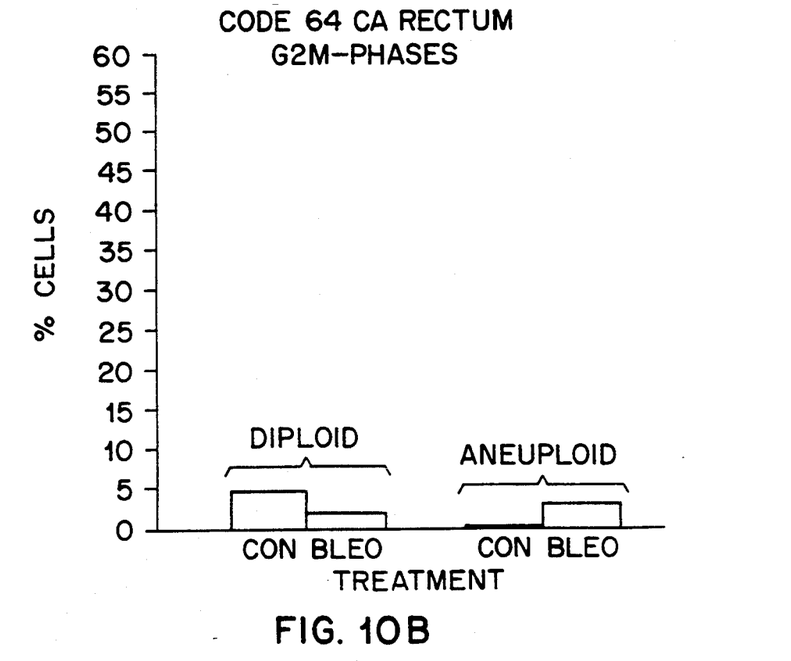

FIG. 10 shows results from drug treatments with Bleo on an adenocarcinoma of the rectum. GSH values in the tumor were 30% below normal values. Diploid tumor cells exhibited an increase in S-phase cells and a decrease in $G_2M$ phase cells. Aneuploid cells showed an 85-fold reduction in S-phase cells ($G_1$ block), and a $G_2M$ block.

These 4 tumors treated with one or more anticancer drugs exhibited a range of responses to treatment. Since all the tumors had normal or lower ranges of GSH, no resistance was observed.

The assay method of the present invention provides a rapid test (complete within 72-96 hours) which is performed on the biopsy or leukemia sample from specific patients to be treated. By combining the results of up to nine different interrelated and confirmatory assay, i.e.

(1) drug effects on cell kinetics via flow cytometry;
(2) baseline GSH values to predict and confirm resistance;
(3) baseline PGP values to predict and confirm resistance;
(4) BSO-inhibition of GSH synthesis and activity, thereby causing reversal of resistance;
(5) calcium channel blocker (Verapamil) inhibition of PGP activity, allowing reversal of resistance;
(6) cytokeratin antibody counterstain to allow assays to be performed specifically on tumor cells;
(7) BrdU antibody counterstain to provide alternative means of assessing drug effects on DNA synthesis;
(8) DNA Index; and
(9) % S-phase and proliferation fraction improved reliability is obtained. Furthermore, tests such as the DDS assay allows the addition of other tests, such as Estrogen Receptor/Progesterone Receptor, Cathepsin-D, oncogenes; for topoisomerase (possibly associated with resistance through repair of drug-induced damage); polyamines (associated with tumor cell growth and differentiation) can also be incorporated to enhance the customerization of the assay results to the individual patient.

TABLE 1

| Drug Effects on Cell Kinetics (% S-phase cells) | GSH Values in Untreated Cells | BSO-Induced Decrease in GSH | Drug Effects After BSO Treatment |
|---|---|---|---|
| Drug A: | | | |
| No change from control (from wells A1–A3) | 2× above normal (determined from difference between well 2 and normal tissue assays) | Reduced to normal (from control wells 4, 5 & 6 and baselines) | 3 fold increase in % S-phase (wells A4–A6) |
| Drug B: | | | |
| 4–5 fold increase in S-phase | 2× above normal | Reduced to normal | No change |

TABLE 2

| Drug Effects on Cell Kinetics (% S-phase cells) | PGP Values in Untreated Cells | Verapamil-Induced Decrease in PGP | Drug Effects After Verapamil Treatment |
|---|---|---|---|
| Drug C: | | | |
| No increase in S-phase | 3× above normal | Reduced to normal | 3–4 fold increase in % S-phase fraction |
| Drug D: | | | |
| 4–5 fold increase in S-phase | 3× above normal | Reduced to normal | No change |

What is claimed is:

1. A method of screening tumor tissue of a patient for susceptibility or resistance to chemotherapy agents using tumor cell kinetics as an indicator thereof, comprising the steps of:
   (a) obtaining a sample of normal tissue and a sample of tumor tissue from the patient:
   (b) measuring the baseline level of glutathione in a portion of each of the two samples;
   (c) dissociating a further portion of the tumor sample into 1–3 mm³ fragments and suspending the dissociated tumor tissue in tissue culture medium;
   (d) dispensing suspended tumor tissue into a plurality of vessels;
   (e) pretreating the suspended tumor tissue in a first portion of the vessels from step (d) by adding buthionine sulfoximine thereto and incubating under conditions suitable for cell growth for a period of time sufficient to achieve 80–90% reduction in GSH;
   (f) incubating a second portion of the vessels from step (d) for the same amount of time as the first portion of vessels is incubated in step (e).

(g) adding a chemotherapy agent to a portion of the vessels containing the pretreated dissociated tumor tissue following incubation in step (e), the remainder of the vessels from step (e) and the vessels from step (f) serving as controls;

(h) incubating the suspended tumor tissue in the presence of the chemotherapy agent from step (g) for a further period of time sufficient to achieve an effect on cell cycle kinetics;

(i) incubating the controls from step (g) for the same amount of time as the suspended tumor tissue in the presence of the chemotherapy agent is incubated in step (h).

(j) recovering the suspended tumor tissue after incubation in steps (h) and (i); and (k) evaluating the effects of the chemotherapy agent on tumor cells from the tumor tissue in the presence and absence of buthionine sulfoximine pretreatment whereby the effectiveness of the chemotherapy agent against the tumor cells and the desirability of pretreatment to reduce levels of glutathione may be determined.

2. A method according to claim 1, further comprising the steps of:

(l) measuring the baseline level of p-glycoprotein in a portion of each of the two samples from step (a):

(m) pretreating the suspended tumor tissue in a third portion of the vessels from step (d) by adding a calcium channel blocker thereto and incubating under conditions suitable for cell growth for a period of time sufficient to achieve 80–90% reduction in PGP content;

(n) incubating a fourth portion of the vessels from step (d) for the same amount of time as the second portion of vessels is incubated in step (m);

(o) adding the chemotherapy agent to a portion of the vessels containing the pretreated dissociated tumor tissue following incubation in step (m), the remainder of the vessels from step (m) and the vessels from step (n) serving as controls;

(p) incubating the suspended tumor cells in the presence of the chemotherapy agent from step (o) for a further period of time sufficient to achieve an effect on cell cycle kinetics;

(q) incubating the controls from step (o) for the same amount of time as the suspended tumor tissue in the presence of the chemotherapy agent is incubated in step (p);

(r) recovering the suspended tumor tissue after incubation in steps (p) and (q); and (s) evaluating the effects of the chemotherapy agent on the tumor cells from the tumor tissue in the presence and absence of calcium channel blocker pretreatment, whereby the effectiveness of the chemotherapy agent against the tumor cells and the desirability of pretreatment to reduce levels of p-glycoprotein may be determined.

3. A method according to claim 2, wherein the calcium channel blocker is Verapamil.

4. A method according to claim 1 or 2, wherein the cells are stained with a fluorescent DNA stain following incubation with the chemotherapy agent and the S-phase and proliferation fractions are then determined by flow cytometry.

5. A method according to claim 4, wherein the stained cells are further counterstained prior to flow cytometry analysis to distinguish cancer from normal cells.

6. A method according to claim 5, wherein the cells are counterstained with cytokeratin.

7. A method according to claim 2, wherein the calcium channel blocker is Verapamil.

8. A method according to claim 1 or 2, further comprising the step of measuring the amount of DNA synthesized by tumor cells in the presence and absence of chemotherapeutic agent.

9. A method according to claim 8, wherein the cells are stained with a fluorescent DNA stain following incubation with the chemotherapy agent and the S-phase and proliferation fractions are then determined by flow cytometry.

10. A method according to claim 9, wherein the stained cells are further counterstained prior to flow cytometry analysis to distinguish cancer from normal cells.

11. A method according to claim 10, wherein the cells are counterstained with cytokeratin.

12. A method according to claim 2, wherein the calcium channel blocker is Verapamil.

* * * * *